United States Patent [19]

Yamamoto et al.

[11] Patent Number: 5,714,655
[45] Date of Patent: Feb. 3, 1998

[54] PROCESS OF MANUFACTURING 1,1,1,3,3-PENTAFLUOROPROPANE, PROCESS OF MANUFACTURING 2,2,3-TRICHLORO 1,1,1,3,3-PENTAFLUOROPROPANE AND PROCESS OF MANUFACTURING 2,3,3-TRICHLORO-1,1,1-TRIFLUOROPROPENE

[75] Inventors: Akinori Yamamoto; Eiji Seki; Hirokazu Aoyama; Seiji Takubo; Tatsuo Nakada, all of Settsu, Japan

[73] Assignee: Daikin Industries, Ltd., Osaka, Japan

[21] Appl. No.: 549,815

[22] PCT Filed: May 30, 1994

[86] PCT No.: PCT/JP94/00867

§ 371 Date: Dec. 8, 1995

§ 102(e) Date: Dec. 8, 1995

[87] PCT Pub. No.: WO94/29252

PCT Pub. Date: Dec. 22, 1994

[30] Foreign Application Priority Data

Jun. 10, 1993 [JP] Japan ........................... 5-165233
Dec. 29, 1993 [JP] Japan ........................... 5-349734

[51] Int. Cl.⁶ .......................... C07C 17/087; C07C 17/20
[52] U.S. Cl. ........................... 570/176; 570/160; 570/170
[58] Field of Search ............................ 570/176, 170, 570/160

[56] References Cited

U.S. PATENT DOCUMENTS 2,558,703  6/1951  Gochenour .
2,942,036  6/1960  Smith et al. .
5,057,634  10/1991 Webster et al. .
5,068,472  11/1991 Webster et al. .
5,315,048  5/1994  VanDerPuy et al. ............... 570/176
5,364,992  11/1994 Manogue et al. ................... 570/176
5,488,189  1/1996  Sievert et al. ...................... 570/176

FOREIGN PATENT DOCUMENTS 0 434 408  6/1991  European Pat. Off. .
0 434 409  6/1991  European Pat. Off. .
4-108746   4/1992  Japan .
4-145033   5/1992  Japan .

*Primary Examiner*—C. Warren Ivy
*Assistant Examiner*—Lyman H. Smith
*Attorney, Agent, or Firm*—Armstrong, Westerman, Hattori, McLeland & Naughton

[57] ABSTRACT

2,2,3-trichloro-1,1,1,3,3-pentafluoropropane is used as a raw material, to which not less than 4.5 equivalent parts of hydrogen are added to effect a hydrogenation reaction in the presence of a noble metal catalyst, particularly a palladium catalyst, by the vapor phase method to manufacture 1,1,1,3,3-pentafluoropropane. Further, propane, propene, and hexachloropropene, etc. are chlorofluorinated in the presence of a metal catalyst to produce 2,2,3-trichloro-1,1,1,3,3-pentafluoropropane, then this compound is reduced with hydrogen in the presence of a noble metal catalyst to produce 1,1,1,3,3-pentafluoropropane. 2,2,3-trichloro-1,1,1,3,3-pentafluoropropane and 1,1,1,3,3-pentafluoropropane can thus be efficiently and economically produced.

19 Claims, No Drawings

PROCESS OF MANUFACTURING 1,1,1,3,3-PENTAFLUOROPROPANE, PROCESS OF MANUFACTURING 2,2,3-TRICHLORO 1,1,1,3,3-PENTAFLUOROPROPANE AND PROCESS OF MANUFACTURING 2,3,3-TRICHLORO-1,1,1-TRIFLUOROPROPENE

This application is a 35 USC 371 National Stage filing of PCT/JP94/00867 published as WO94/29252 on Dec. 22, 1994.

INDUSTRIAL USE

This invention pertains to the process of manufacturing 1,1,1,3,3-pentafluoropropane (HFC245fa), a useful compound which may become a substitute compound for CFC and HCFC used as refrigerant, blowing agent and cleaner, in more detail to the process of manufacturing 1,1,1,3,3-pentafluoropropane with 2,2,3-trichloro-1,1,1,3,3-pentafluoropropane (CFC215aa) as an intermediate, to the process of manufacturing 2,2,3-trichloro-1,1,1,3,3-pentafluoropropane (CFC215aa), an intermediate of HFC245fa, and to the process of manufacturing 2,3,3-trichloro-1,1,1-trifluoropropene, an intermediate of CFC215aa.

PRIOR ART 1,1,1,3,3-pentafluoropropane (HFC245fa) is a useful compound as a substitute for freon used as a blowing agent, refrigerant, cleaner, etc.

As the process of manufacturing 1,1,1,3,3-pentafluoropropane (HFC245fa), a method is known under which 2,2,3-trichloro-1,1,1,3,3-pentafluoropropane (CFC215aa) is used as a raw material, which is reduced with a palladium catalyst supported on activated carbon using 1.5 to 4 mols of hydrogen to the raw material (U.S. Pat. No. 2,942,036).

Manufacturing HFC245fa using CFC215aa involves two broad categories of problems. The first problem is how efficiently and economically CFC215aa is manufactured, and the second problem is how efficiently CFC215aa is reduced to obtain HFC245fa.

Regarding the first problem, it is important to select a low-priced starting material and to efficiently convert it into CFC215aa. There have been several reports on techniques of using low-price available compound with carbon number of 3 as a starting material, then chlorine-fluorinating it to obtain $CF_3 CFClCF_3$.

Japanese Patent Opening No. 145033/92 discloses a process of manufacturing $CF_3 CFClCF_3$ in which propane and propylene, etc. are chlorofluorinated to generate a perhalogenated C3 chlorofluoro compound, and this compound is fluorinated. Japanese Patent Opening No. 117335/92 discloses a process in which propane and propylene, etc. are chlorine-fluorinated to generate $CF_3 CCl=CCl_2$, and this compound is further chlorine-fluorinated to form $CF_3 CFClCF_3$. Japanese Patent Opening No. 108746/92 discloses a process in which hexachloropropene is chlorofluorinated to generate a perhalogenated $C_3$ chlorofluoro compound and this compound is fluorinated to form $CF_3 CFClCF_3$.

However, these processes are designed to obtain $CF_3 CFClCF_3$ (a $C_3$ compound with 7 fluorine atoms and 1 chlorine atom), and the application of these processes to the manufacture of $CF_3 CCl_2 CF_2 Cl$ (a $C_3$ compound with 5 fluorine atoms and 3 chlorine atoms) (CFC215aa) produces a large amount of by-product which are too fluorinated, thus not only producing a low yield rate, but also making it impossible to reuse the by-product as a raw material for manufacturing CFC215aa. A method of synthesizing the conditions suitable for the manufacture of CFC215aa therefore needs to be developed.

Regarding the second problem, that is, the reduction of CFC215aa, the above U.S. patented process provides only a maximum 60% yield rate to HFC245fa, the subject-matter, and also produces a large amount of 1,1,3,3,3-pentafluoropropene, which is not suitable for industry. Consequently, an efficient process of reducing CFC215aa into HFC245fa needs to be developed.

OBJECT OF INVENTION

The object of this invention is to provide a process to efficiently and economically manufacture 1,1,1,3,3-pentafluoropropane, especially a process of manufacturing 1,1,1,3,3-pentafluoropropane at a high yield rate in the reductive reaction of 2,2,3-trichloro-1,1,1,3,3-pentafluoropropane.

The other object of this invention is to provide a process to efficiently and economically manufacture 2,2,3-trichloro-1,1,1,3,3-pentafluoropropane and 2,3,3-trichloro-1,1,1-trifluoropropene as intermediates in the manufacture of 1,1,1,3,3-pentafluoropropane.

CONSTITUTION OF INVENTION

This inventors have investigated in detail the process of manufacturing 1,1,1,3,3-pentafluoropropane, and have discovered that the reduction of 2,2,3-trichloro-1,1,1,3,3-pentafluoropropane, when used as a raw material as in the past at not more than 4 equivalent parts of hydrogen by the vapor phase method in the presence of a noble metal catalyst, especially a palladium catalyst, provides the subject-matter at a low yield rate, while reduction using not less than 4.5 equivalent parts of hydrogen provides the subject-matter at a high yield and selection rates, thus leading to completion of the present invention.

This invention pertains to the process of manufacturing 1,1,1,3,3-pentafluoropropane, including a process in which 2,2,3-trichloro-1,1,1,3,3-pentafluoropropane is allowed to react with not less than 4.5 equivalent parts of hydrogen to 2,2,3-trichloro-1,1,1,3,3-pentafluoropropane to be hydrogen-reduced by the vapor phase method in the presence of a noble metal catalyst.

In the manufacturing process based on this invention, 2,2,3-trichloro-1,1,1,3,3-pentafluoropropane in particular is used as the raw material, to which not less than 4.5 equivalent parts (particularly 4.5 to 10 equivalent parts) of hydrogen is used to allow to react with hydrogen added particularly at temperatures of 100° C. to 350° C. by the vapor phase method in the presence of a palladium catalyst, which permits the manufacture of 1,1,1,3,3-pentafluoropropane at a high yield rate of 90% or more.

The usable vapor phase reaction methods include the fixed bed vapor phase reaction method and the fluidized bed vapor phase reaction method.

It is preferable that the palladium catalyst is supported on a carrier composed of at least one carrier selected from among activated carbon, alumina, silica gel, titanium oxide and zirconia.

The grain size of the carrier hardly affects the reaction, but a size of 0.1 mm to 100 mm is preferred.

The usable range of supporting concentrations varies widely from 0.05% to 10% by weight, but usually a carrier at 0.5% to 5% by weight is recommended.

The reaction temperature is normally 100° C. to 350° C., preferably 200° C. to 300+ C.

According to the present invention, when 2,2,3-trichloro-1,1,1,3,3-pentafluoropropane is reduced with hydrogen, the amount of hydrogen can vary widely, but not less than 4.5 mols of hydrogen should be used per mol of 2,2,3-trichloro-1,1,1,3,3-pentafluoro-propane. Usually, 1.5 to 3 times as much hydrogen than the stochiometric amount is used to ensure hydrogenation. A considerably greater amount of hydrogen, 10 mols or more, for example, may be used. Excess hydrogen can be recovered and reused.

The reaction pressure is not particularly restricted, and applied pressure, reduced pressure, and atmospheric pressure may be used, but reaction under applied or atmospheric pressure is preferred.

The contact time is usually 0.1 s to 300 s, typically 1 s to 30 s.

This invention also provides a process of manufacturing 1,1,1,3,3-pentafluoropropane including processes (1) and (2) as follows:

(1) A process in which hexachloropropene is allowed to react with hydrogen fluoride (HF) and chlorine in the presence of a chromium or aluminum catalyst by the vapor phase method, or in the presence of an antimony catalyst by the liquid phase method to obtain 2,2,3-trichloro-1,1,1,3,3-pentafluoropropane.

(2) Then, a process in which this 2,2,3-trichloro-1,1,1,3,3-pentafluoropropane is allowed to react with not less than 4.5 equivalent parts of hydrogen to this 2,2,3-trichloro-1,1,1,3,3-pentafluoropropane to be hydrogen-reduced in the presence of a noble metal catalyst by the vapor phase method, obtaining 1,1,1,3,3-pentafluoropropane.

This invention also provides the process of manufacturing 1,1,1,3,3-pentafluoropropane including processes (1), (2) and (3) as follows:

(1) A process in which hexachloropropene is allowed to react with hydrogen fluoride (HF) in the presence of an aluminum catalyst by the vapor phase method to obtain 2,3,3-trichloro-1,1,1-trifluoropropene.

(2) Then, a process in which this 2,3,3-trichloro-1,1,1-trifluoropropene is allowed to react with hydrogen fluoride (HF) and chlorine in the presence of at least one metal catalyst selected from a group composed of chromium, iron, cobalt, zinc, copper and manganese by the vapor phase method, or in the presence of an antimony catalyst by the liquid phase method to obtain 2,2,3-trichloro-1,1,1,3,3-pentafluoropropane.

(3) Then, a process in which this 2,2,3-trichloro-1,1,1,3,3-pentafluoropropane is allowed to react with not less than 4.5 equivalent parts of hydrogen to 2,2,3-trichloro-1,1,1,3,3-pentafluoropropane in the presence of a noble metal catalyst by the vapor phase method to be hydrogen-reduced, obtaining 1,1,1,3,3-pentafluoropropane.

This invention also provides the process of manufacturing 1,1,1,3,3-pentafluoropropane including processes (1) and (2) as follows:

(1) A process in which at least a kind selected from a group composed of 2,3,3-trichloro-1,1,1-trifluoropropene, 1,2,3,3-tetrachloro-1,1-difluoropropene, and 1,1,2,3,3-pentachloro-1-fluoropropene is allowed to react with hydrogen fluoride (HF) and chlorine in the presence of at least one metal catalyst selected from a group composed of chromium, iron, cobalt, zinc, copper and manganese by the vapor phase method, or in the presence of an antimony catalyst by the liquid phase method to obtain 2,2,3-trichloro-1,1,1,3,3-pentafluoropropane.

(2) Then, a process in which this 2,2,3-trichloro-1,1,1,3,3-pentafluoropropane is allowed to react with not less than 4.5 equivalent parts of hydrogen to 2,2,3-trichloro-1,1,1,3,3-pentafluoropropane to be hydrogen-reduced by the vapor phase method in the presence of a noble metal catalyst, obtaining 1,1,1,3,3-pentafluoropropane.

This invention also provides a process of manufacturing 1,1,1,3,3-pentafluoropropane including processes (1) and (2) as follows:

(1) A process in which at least one compound selected from a group composed of propane, propylene, and partially halogenated an acyclic hydrocarbon with a carbon number of 3 is allowed to react with hydrogen fluoride (HF) and chlorine in the presence of chromium and/or iron catalyst(s) by the vapor phase method to obtain 2,2,3-trichloro-1,1,1,3,3-pentafluoropropane.

(2) Then, a process in which this 2,2,3-trichloro-1,1,1,3,3-pentafluoropropane is allowed to react with not less than 4.5 equivalent parts of hydrogen to 2,2,3-trichloro-1,1,1,3,3-pentafluoropropane in the presence of a noble metal catalyst by the vapor phase method to be hydrogen-reduced, obtaining 1,1,1,3,3-pentafluoropropane.

This invention also provides a process of manufacturing 1,1,1,3,3-pentafluoropropane including processes (1), (2) and (3) as follows:

(1) A process in which at least one compound selected from a group composed of propane, propylene and partially halogenated acyclic hydrocarbon with carbon number of 3 is allowed to react with hydrogen fluoride (HF) and chlorine in the presence of at least one metal catalyst selected from a group composed of aluminum, copper, cobalt, zinc and manganese by the vapor phase method to obtain 2,3,3-trichloro-1,1,1-trifluoropropene.

(2) Then, a process in which this 2,3,3-trichloro-1,1,1-trifluoropropene is allowed to react with hydrogen fluoride (HF) and chlorine in the presence of at least one metal catalyst selected from a group composed of chromium, iron, cobalt, zinc, copper and manganese by the vapor phase method, or in the presence of an antimony catalyst by the liquid phase method to obtain 2,2,3-trichloro-1,1,1,3,3-pentafluoropropane.

(3) Then, a process in which this 2,2,3-trichloro-1,1,1,3,3-pentafluoropropane is allowed to react with not less than 4.5 equivalent parts of hydrogen to 2,2,3-trichloro-1,1,1,3,3-pentafluoropropane to be hydrogen-reduced in the presence of noble metal catalyst(s) by the vapor phase method, obtaining 1,1,1,3,3-pentafluoropropane.

This invention also provides a process of manufacturing 2,2,3-trichloro-1,1,1,3,3-pentafluoropropane including a process in which hexachloropropene is allowed to react with hydrogen fluoride (HF) and chlorine in the presence of chromium and/or aluminum catalyst(s) by the vapor phase method, or in the presence of an antimony catalyst by the liquid phase method.

This invention also provides a process of manufacturing 2,2,3-trichloro-1,1,1,3,3-pentafluoropropane including processes (1) and (2) as follows:

(1) A process in which hexachloropropene is allowed to react with hydrogen fluoride (HF) in the presence of an aluminum catalyst by the vapor phase method to obtain 2,3,3-trichloro-1,1,1-trifluoropropene.

(2) Then, a process in which this 2,3,3-trichloro-1,1,1-trifluoropropene is allowed to react with hydrogen fluoride (HF) and chlorine in the presence of at least one metal catalyst selected from a group composed of chromium, iron, cobalt, zinc, copper and manganese by the vapor phase method, or in the presence of an antimony catalyst by the liquid phase method to obtain 2,2,3-trichloro-1,1,1,3,3-pentafluoropropane.

This invention also provides a process of manufacturing 2,2,3-trichloro-1,1,1,3,3-pentafluoropropane including a process in which at least one selected from a group composed of 2,3,3-trichloro-1,1,1-trifluoropropene, 1,2,3,3-tetrachloro-1,1-difluoropropene and 1,1,2,3,3-pentachloro-1-fluoropropene is allowed to react with hydrogen fluoride (HF) and chlorine in the presence of at least one metal catalyst selected from a group composed of chromium, iron, cobalt, zinc, copper and manganese by the vapor phase method, or in the presence of an antimony catalyst by the liquid phase method to obtain 2,2,3-trichloro-1,1,1,3,3-pentafluoropropane.

This invention further provides a process of manufacturing 2,3,3-trichloro-1,1,1-trifluoropropene, including a process in which hexachloropropene is allowed to react with hydrogen fluoride (HF) in the presence of an aluminum catalyst by the vapor phase method.

In the above processes of manufacturing on the basis of this invention, the following preferable routes may be adopted in order to obtain CFC215aa as an intermediate in manufacturing 1,1,1,3,3-pentafluoropropane (HFC245fa) by manufacturing 2,2,3-trichloro-1,1,1,3,3-pentafluoropropane (CFC215aa) first, and then hydrogen-reducing the compound.

Method A

Hexachloropropene is used as the starting substance, and this compound is allowed to react with HF and chlorine to be chlorofluorinated, obtaining CFC215aa directly.

Method B

Hexachloropropene is used as the starting substance, and this compound is allowed to react with HF to be fluorinated, generating 2,3,3-trichloro-1,1,1-trifluoropropene, then the compound is allowed to react with HF and chlorine to be chlorofluorinated, obtaining CFC215aa.

Method C

At least one selected from a group composed of 2,3,3-trichloro-1,1,1-trifluoropropene, 1,2,3,3-tetrachloro-1,1-difluoropropene, and 1,1,2,3,3-pentachloro-1-fluoropropene is used as the starting substance, and this compound is chlorofluorinated with HF and chlorine to obtain CFC215aa.

Method D

Propane, propylene and/or partially halogenated acyclic hydrocarbon with carbon number of 3 is used as the starting substance, and this compound is allowed to react with HF and chlorine to be chlorofluorinated, obtaining CFC215aa directly.

Method E

Propane, propylene and/or partially halogenated acyclic hydrocarbon with carbon number of 3 is used as the starting substance, and this compound is allowed to react with HF and chlorine to be chlorofluorinated first, generating 2,3,3-trichloro-1,1,1-trifluoropropene, then the compound is allowed to react with HF and chlorine to be chlorofluorinated, obtaining CFC215aa.

In Method A, hexachloropropene is used as the starting substance to be chlorofluorinated with hydrogen fluoride and chlorine, either by the vapor phase method or the liquid phase method.

The catalyst in the vapor phase method includes chromium and/or aluminum. These catalysts can be used in the form of a salt such as the hydroxide, chloride, nitrate or oxide of the metal. These catalysts can also be used in a condition where the above metals are supported on a carrier such as activated carbon. The supporting quantity of metal catalyst on the carrier is not particularly restricted, but preferably not less than 0.1% by weight. The supporting method on the carrier in general is such that a metal compound normally in the form of a water soluble salt such as nitrate is dissolved in the ion-exchanged water in which the carrier is soaked, and the water content is removed by distillation to obtain the desired catalyst.

The catalyst is preferably be treated for fluorination prior to starting the reaction. A preferable fluorination method is to bring the catalyst into contact with HF at a temperature not less than that provided for reaction, but an excessively high temperature will reduce the activity of the catalyst. The reaction temperature must therefore be set properly and at the same time HF must be diluted with nitrogen, etc. to control the temperature elevation resulting from the fluorination reaction. Generally, the fluorination temperature ranges from 200° C. to 400° C. An aluminum catalyst, particularly with alumina as the material, is preferably be fluorinated until the fluorine content reaches around 50% to 80% ($AlF_3$ standards). When used in reaction at higher temperatures, fluorination up to about 90% is suggested.

In the chlorine fluorination reaction of hexachloropropene, the mol ratio of hexachloropropene to hydrogen fluoride is 1:1 to 1:100, preferably 1:5 to 1:50, and the mol ratio of hexachloropropene to chlorine is 1:1 to 1:30, preferably 1:1 to 1:20.

The usable vapor phase reaction methods include the fixed bed vapor phase reaction method and the fluidized vapor phase reaction method.

The reaction temperature may be 50° C. to 500° C., normally 100° C. to 500° C., and preferably 150° C. to 400° C.

Reaction is practicable either atmospheric, reduced, or applied pressure conditions, but reaction under atmospheric or applied pressure conditions is preferred to reduce equipment complexity.

The optimum contact time of hexachloropropene with the catalyst, which depends upon other conditions, is 0.1 s to 100 s.

In the chlorofluorination of hexachloropropene, $CF_3 CCl_2 CF_2 Cl$ is the target compound, but $CF_3 CCl_2 CCl_2 F$, $CF_3 CCl=CFCl$, $CF_3 CCl=CCl_2$, compounds which are insufficiently chlorofluorinated, may also be obtained as by-products. Further chlorofluorination can convert these compounds into the intended $CF_3 CCl_2 CF_2 Cl$. Consequently, these by-products can be reused by returning them to the reaction system.

In the liquid phase method in Method A, chlorofluorinated antimony may be used as a catalyst. chlorofluorinated antimony used in this reaction can be prepared either by reacting antimony pentachloride with hydrogen fluoride to be partially fluorinated, or by reacting antimony trifluoride with chlorine. The fluorine content in halogenated antimony depends upon the reaction conditions, irrespective of the preparation method.

Five-fold mols of HF used in the reaction to hexachloropropene are required theoretically, and reaction is still practicable with five-fold mols; however, in order to improve the reaction it is necessary to increase the reaction quantity of HF in the range from five-fold to ten-fold mols. However, excess HF must be recovered as an unreacted product, and hence the use of HF beyond this range is disadvantageous in terms of cost although the reaction is not affected.

Equivalent mols of chlorine used in the reaction to hexachloropropene are necessary theoretically, and reaction is still practicable with equivalent mols; however, in order to improve the reaction, 1.2 to 3 times as many mols of chlorine is desired be used. In the same way as HF, however, excess chlorine must be recovered as an unreacted product, and hence the introduction of chlorine beyond this range is disadvantageous in terms of cost although the reaction is not affected.

The reaction temperature may not be less than 50° C., but since the reaction velocity increases at higher reaction temperature, the reaction is preferably be performed at 80° C. or higher. However, the temperature must not be too high, otherwise corrosion-resistant materials are required for the reactor. Generally, the reaction is performed at 150° C. or below.

Reaction is practicable at atmospheric pressure as well, but is preferably be performed under pressurized conditions in the range of 8 to 20 kg/cm$^2$ since in the chlorine fluorination reaction by antimony, the hydrochloric acid generated is generally separated from HF.

In Method B, hexachloropropene is first allowed to react first with HF by the vapor phase method to be fluorinated, obtaining 2,3,3-trichloro-1,1,1-trifluoropropene.

Aluminum is well suited as the catalyst in this reaction.

The catalyst can be used in the form of a salt such as the hydroxide, chloride, nitrate, or oxide of aluminum. The catalyst can also be used such that the above aluminum compounds are supported on a carrier such as activated carbon. The supporting quantity of the aluminum catalyst on the carrier is not particularly restricted, but should not be less than 0.1% by weight. The supporting method on the carrier is usually such that an aluminum compound in the form of a water soluble salt such as nitrate is dissolved in the ion-exchanged water in which the carrier is soaked, and the water content is removed by distillation to obtain the desired catalyst.

The catalyst is preferably be treated for fluorination prior to starting the reaction. The fluorination treatment method is as mentioned above.

In the fluorination reaction of hexachloropropene, the mol ratio of hexachloropropene to hydrogen fluoride is 1:1 to 1:100, and preferably 1:3 to 1:50.

The usable vapor phase reaction methods include the fixed bed vapor phase reaction method and the fluidized bed vapor phase reaction method.

The reaction temperature is 100° C. to 500° C., preferably 150° C. to 400° C.

Reaction is practicable under the atmospheric, reduced and applied pressure conditions, while reaction under atmospheric or applied pressure conditions is preferred to reduce equipment complexity.

The contact time of perchloropropene with the catalyst, which depends upon the other conditions, is usually 0.1 s to 100 s.

In Method B, 2,3,3-trichloro-1,1,1-trifluoropropene thus obtained is allowed to react with HF and chlorine either by the vapor phase method or the liquid phase method to be chlorofluorinated, obtaining 2,2,3-trichloro-1,1,1,3,3-pentafluoropropane.

The catalyst used in the vapor phase method includes chromium, iron, cobalt, zinc, copper and manganese. Two or more of these metals may be mixed for use. These catalysts may also be used in the form of a salt such as the hydroxide, chloride, nitrate, or oxide of the metal. These catalysts can also be used in a condition where the above metals are supported on a carrier such as activated carbon or alumina, etc. The suitable supporting quantity of the metal catalyst on the carrier, which is not particularly restricted, preferably not be less than 0.1% and not more than 50% by weight. The supporting method on the carrier is usually such that a metal compound in the form of a water soluble salt such as nitrate is dissolved in the ion-exchanged water in which the carrier is soaked, then the water content is removed by distillation to obtain the desired catalyst. The catalyst is preferably be fluorination-treated before being used in the reaction. The fluorination treatment method is as mentioned above.

The mol ratio of 2,3,3-trichloro-1,1,1-trifluoropropene to hydrogen fluoride is 1:1 to 1:50, preferably 1:2 to 1:30, and that of 2,3,3-trichloro-1,1,1-trifluoropropene to chlorine is 1:1 to 1:30, preferably 1:1 to 1:20

The usable vapor phase methods include the fixed bed vapor phase reaction method and the fluidized bed vapor phase reaction method.

The reaction temperature may be 50° C. to 500° C., normally 100° C. to 500° C., and preferably 150° C. to 450° C.

Reaction is practicable under atmospheric, reduced and applied pressure conditions, but reaction under atmospheric or applied pressure conditions is preferred to reduce equipment complexity.

The contact time of the reaction substrate with the catalyst, which depends upon the other conditions, is usually 0.01 s to 100 s.

$CF_3 CCl_2 CCl_2 F$, $CF_3 CCl=CFCl$ may be generated as by-products, which can be reused by returning to the reaction system.

In the liquid phase method, chlorofluorinated antimony may be used. Chlorofluorinated antimony used in this reaction can be prepared either by reacting hydrogen fluoride with antimony pentachloride to be partially fluorinated, or reacting antimony trifluoride with chloride. The fluorine content in halogenated antimony depends upon the reaction conditions irrespective of the preparation method.

The mol ratio of 2,3,3-trichloro-1,1,1-trifluoropropene to hydrogen fluoride is 1:2 to 1:4, preferably 1:2.4 to 1:3, and the mol ratio of 2,3,3-trichloro-1,1,1-trifluoropropene to chlorine is 1:1 to 1:3, preferably 1:1.2 to 1:1.5.

The reaction temperature may not be less than 50° C., but since the reaction velocity increases at higher reaction temperature, the reaction is preferably be performed at 80° C. or higher. However, the temperature must not be too high, otherwise corrosion-resistant materials are required for the reactor. Generally, the reaction is performed at 150° C. or below.

Reaction is practicable at atmospheric pressure as well, but is preferably be performed under the pressurized conditions in the range of 8 to 20 kg/cm$^2$ since in the fluorination reaction by antimony, hydrochloric acid generated is generally separated from HF.

The reaction time, which also depends on the reaction temperature, is usually 1 to 3 hours.

In Method C, at least one of 2,3,3-trichloro-1,1,1-trifluoropropene, 1,2,3,3-tetrachloro-1,1-difluoropropene, and 1,1,2,3,3-pentachloro-1-fluoropropene is used as the starting substance. This compound is then allowed to react with HF and chlorine to be chlorofluorinated, obtaining 2,2,3-trichloro-1,1,1,3,3-trifluoropropane. The reaction conditions of the chlorofluorination are the same as those under which 2,2,3-trichloro-1,1,1,3,3-trifluoropropane is obtained from 2,3,3-trichloro-1,1,1-trifluoropropene in the above Method B.

In Method D, propane, propylene, and/or partially halogenated acrylic hydrocarbons with 3 carbons is used as the starting substance. This is then allowed to react with HF and chlorine to be chlorofluorinated by the vapor phase method, obtaining CFC215aa directly. Examples of partially halogenated acyclic hydrocarbons with 3 carbons include allylchloride, isopropylohloride, 1,1,1-trifluoro-2-propene, and 1,1,1,3,3,3-hexachloropropane.

The catalyst for this reaction includes metallic chromium and iron, a mixture of which may be used. These catalysts can be used in the form of a salt such as hydroxide, chloride, nitrate, or the oxide of the metal. In addition, these catalysts can be used by carrying the above metals on a carrier such as active carbon or alumina. The quantity of the metal catalyst on the carrier is not particularly restricted, but should not be less than 0.1% and not more than 50% by weight. The carrying method on the carrier is usually such that a metal compound in the form of a water soluble salt such as nitrate is dissolved in ion-exchanged water, in which the carrier is soaked, then the water content is removed by distillation to obtain the desired catalyst. The catalyst should be fluorinated prior to use in the reaction. The fluorination treatment process is as described above.

In the chlorofluorination reaction of propane, propylene, and/or partially halogenated acyclic hydrocarbon, with 3 carbons, the mole ratio of the reaction substrate to hydrogen fluoride is 1:5 to 1:100, preferably 1:5 to 1:50, and that of the reaction substrate to chlorine is 1:5 to 1:30, preferably 1:5 to 1:20.

The usable vapor phase reaction method includes the fixed bed vapor phase reaction method and the fluidized bed vapor phase reaction method.

The reaction temperature may be from 50° C. to 500° C., usually 100° C. to 500° C., and preferably 150° C. to 450° C.

Reaction is possible at atmospheric, reduced or applied pressure, but reaction at atmospheric or applied pressure is preferred to reduce equipment complexity.

A suitable contact time of the reaction substrate with the catalyst, which varies depending upon the other conditions, is usually 0.01 seconds to 100 seconds.

In the chlorofluorination of propane, propylene, and/or partially halogenated acyclic hydrocarbon having 3 carbons, $CF_3CCl_2CF_2Cl$ is the target compound, while $CF_3CCl_2CCl_2F$, $CF_3CCl=CFCl$, and $CF_3CCl=CCl_2$, compounds that are insufficiently chlorofluorinated, may also be obtained as by-products. These compounds, if further chlorofluorinated, can be converted into the target $CF_3CCl_2CF_2Cl$. Consequently, these by-products can be reused by returning them to the reaction system.

In Method E, propane, propylene, and/or partially halogenated acyclic hydrocarbon having 3 carbons is used as the starting substance. This compound is first allowed to react with HF and chlorine by the vapor phase method to be chlorofluorinated, then 2,3,3-trichloro-1,1,1-trifluoropropene is obtained.

In this reaction, the preferred catalysts are aluminum, copper, cobalt, zinc or manganese, and a mixture of more than one of these metals may be used. These catalysts can be used in the form of a salt such as hydroxide, chloride, nitrate, or the oxide of the metal. In addition, these catalysts can be used by carrying the above metals on a carrier such as active carbon or alumina. The quantity of the metal catalyst on the carrier is not particularly restricted, but desired not be less than 0.1% and not more than 50% by weight. The carrying method on the carrier is usually such that a metal compound in the form of a water soluble salt such as nitrate is dissolved in ion-exchanged water, in which the carrier is soaked, then the water content is removed by distillation to obtain the desired catalyst. The catalyst is preferably fluorinated prior to use in the reaction. The fluorination treatment process is as described above.

In the chlorofluorination reaction of propane, propylene, and/or partially halogenated acyclic hydrocarbon having 3 carbons, the mole ratio of the reaction substrate to hydrogen fluoride is 1:5 to 1:100, preferably 1:5 to 1:50, and that of the reaction substrate to chlorine is 1:5 to 1:30, preferably 1:5 to 1:20.

The usable vapor phase reaction method includes the fixed bed vapor phase reaction method and the fluidized bed vapor phase reaction method.

The reaction temperature may be 50° C. to 500° C., usually 100° C. to 500° C., and preferably 150° C. to 450° C.

Reaction is possible at atmospheric, reduced or applied pressure, but reaction at atmospheric or applied pressure is preferred to reduce equipment complexity.

A suitable contact time of the reaction substrate with the catalyst, which varies depending upon the other conditions, is usually 0.01 seconds to 100 seconds.

In Method E, 2,3,3-trichloro-1,1,1-trifluoropropene obtained is allowed to react with HF and chlorine to be chlorofluorinated, obtaining CFC215aa. The reaction conditions are as described in Method B for the second reaction stage.

2,2,3-trichloro-1,1,1,3,3-pentafluoropropane (CFC215aa) obtained by Methods A to E above is then reduced by reacting it with hydrogen by the vapor phase method, obtaining the target 1,1,1,3,3-pentafluoropropane (HFC245fa).

As the catalyst for the hydrogen reduction reaction of CFC215aa, palladium, platinum and rhodium, etc. are preferred, and a mixture of more than one of these metals may be used. These catalysts can be used in the form of a salt such as hydroxide, chloride, nitrate, or the oxide of the metal. These catalysts can also be used by carrying the above metals on active carbon, alumina, silica gel, titanium oxide or zirconia, etc. The quantity of the metal catalyst on the carrier is not particularly restricted, but suitably not be less than 0.05% and preferably not more than 10% by weight. The grain size of the carrier, which hardly affects the reaction, suitably be 0.1 to 100 mm. The carrying method on the carrier is usually such that a metal compound in the form of a water soluble salt such as nitrate is dissolved in ion-exchanged water, in which the carrier is soaked, then the water content is removed by distillation to obtain the desired catalyst.

The usable vapor phase reaction method includes the fixed bed vapor phase reaction method and the fluidized bed vapor phase reaction method.

In the reduction reaction with hydrogen of 2,2,3-trichloro-1,1,1,3,3-pentafluoropropane on the basis of this invention, the ratio of hydrogen to the raw material may be widely varied provided that the ratio is such that hydrogen is not less than 4.5 equivalent parts (preferably not more than 10 equivalent parts) to 2,2,3-trichloro-1,1,1,3,3-pentafluoropropane. Usually, however, 1.5 to 3 times as much hydrogen as the stoichiometric quantity is used to ensure hydrogenation. Much more quantity, 10 equivalent parts or more, for example, can be used to the total mol of the starting substance. Excess hydrogen can be recovered for reuse.

The reaction temperature is usually from 100° C. to 350° C., preferably from 200° C. to 300° C.

Reaction, whose pressure is not particularly restricted, is possible at applied, reduced or atmospheric pressure, but reaction at applied or atmospheric pressure is preferred.

The contact time is usually 0.1 seconds to 300 seconds, particularly 1 second to 30 seconds.

Industrial potential of invention

According to this invention, since 2,2,3-trichloro-1,1,1,3,3-pentafluoropropane is used as the raw material, to which not less than 4.5 equivalent parts of hydrogen is used to ensure the hydrogenation reaction in the presence of a noble metal catalyst, particularly a palladium catalyst, by the vapor phase method, 1,1,1,3,3-pentafluoropropane can be manufactured at a high yield rate of 90% or more. Thus, since 2,2,3-trichloro-1,1,1,3,3-pentafluoropropane is efficiently reduced to 1,1,1,3,3-pentafluoropropane, 1,1,1,3,3-pentafluoropropane can be efficiently and economically manufactured.

In addition, a starting substance obtainable at a comparatively low cost can be used to obtain 2,2,3-trichloro-1,1,1,3,3-pentafluoropropane at a high yield rate. Many of the generated by-products can be reused as raw materials for manufacturing 2,2,3-trichloro-1,1,1,3,3-pentafluoropropane.

EXAMPLES

This invention is explained in more detail through the following examples but is not necessarily limited by these examples.

Example 1

A SUS-316 reactor tube 7 mm in inside diameter and 150 mm long was filled with 2.3 cc of a palladium catalyst carried on active carbon at 3% concentration. The reactor was heated to 250° C. in an electric furnace while passing nitrogen gas. After the temperature was reached, 2,2,3-trichloro-1,1,1,3,3-pentafluoropropane was introduced at the rate of 1.0 cc/min, together with hydrogen at the rate of 10 cc/min (10 equivalent parts to the raw material). The reaction temperature was kept at 250° C. The produced gas was washed with water and then analyzed by gas chromatography. The results are shown in Table 1.

Example 2

The same reactor as used in Example 1 was filled with 2.3 cc of a palladium catalyst carried on active carbon at 3% concentration. The reactor was heated to 200° C. in an electric furnace while passing nitrogen gas. After the temperature was reached, 2,2,3-trichloro-1,1,1,3,3-pentafluoropropane was introduced at the rate of 1.2 cc/min, together with hydrogen at the rate of 10 cc/min (8.3 equivalent parts to the raw material). The reaction temperature was kept at 200° C. The produced gas was washed with water and then analyzed by gas chromatography. The results are shown in Table 1.

Example 3

The same reactor as used in Example 1 was filled with 2.3 cc of a palladium catalyst carried on active carbon at 3% concentration. The reactor was heated to 200° C. in an electric furnace while passing nitrogen gas. After the temperature was reached, 2,2,3-trichloro-1,1,1,3,3-pentafluoropropane was introduced at the rate of 2.4 cc/min, together with hydrogen at the rate of 12 cc/min (5 equivalent parts to the raw material). The reaction temperature was kept at 200° C. The produced gas was washed with water and then analyzed by gas chromatography. The results are shown in Table 1.

Comparison Example 1

The same reactor as used in Example 1 was filled with 2.3 cc of a palladium catalyst carried on active carbon at 3% concentration. The reactor was heated to 180° C. in an electric furnace while passing nitrogen gas. After the temperature was reached, 2,2,3-trichloro-1,1,1,3,3-pentafluoropropane was introduced at the rate of 2.6 cc/min, together with hydrogen at the rate of 10 cc/min (3.85 mols per mol of the raw material). The reaction temperature was kept at 150° C. The produced gas was washed with water and then analyzed by gas chromatography. The target product 1,1,1,3,3-pentafluoropropane was obtained with a conversion yield of 100% and selectivity of 79.7%.

TABLE 1

| | Conversion (%) | Selectivity (%) |
| --- | --- | --- |
| Example 1 | 100 | 96.8 |
| Example 2 | 100 | 95.9 |
| Example 3 | 100 | 93.5 |
| Comparison example 1 | 100 | 79.7 |

This result shows that the object compound can be obtained with high conversion yield and high selectivity when the reaction is carried out based on the method of this invention.

Example 4

Synthesis of CFC215aa through chlorofluorination of hexachloropropene by the vapor phase method
(1)

First by the following method, $Cr_2 O_3$ was fluorinated. A 20 mm diameter reaction tube made of Hastelloy C was filled with 20 g (15 cc) of $Cr_2 O_3$ in pellet form. It was heated from room temperature, while passing nitrogen and hydrogen fluoride, gradually up to the reaction temperature (350° C.). When the temperature was reached inside the system, the nitrogen was stopped, and when the temperature was stabilized, the next chlorofluorination reaction was started.

Through the reaction tube filled with 20 g of $Cr_2 O_3$, which had been fluorinated, 8.2 cc/min of prevaporized hexachloropropene, 133 cc/min of hydrogen fluoride, and 62 cc/min of chlorine were passed to effect the reaction at 350° C. The produced gas was washed with water, alkali and the water solution of the reducer, and then analyzed by gas chromatography. The results are shown in Table 2.

Example 5

Synthesis of CFC215aa through chlorofluorination of hexachloropropene by the vapor phase method
(2)

First by the following method, $CrCl_3$ was carried on active carbon. 0.45 g of $CrCl_3$ was dissolved in 12 cc of the ion-exchanged water, to which 6 g (14 cc) of active carbon was added. After allowing to stand overnight at room temperature, the water content was removed by an evaporator and then it was allowed to dry another night at 120° C.

It was then fluorinated as follows. The catalyst obtained as above was filled into a 20 mm diameter reaction tube made of Hastelloy C. The tube was heated from room temperature, while passing nitrogen and hydrogen fluoride, gradually up to the reaction temperature (350° C.). When the temperature was reached inside the system, the nitrogen was stopped, and when the temperature was stabilized, the chlorofluorination reaction was started.

Through the reaction tube filled with 6 g of active carbon carrying $CrCl_3$, which had been fluorinated, 11 cc/min of prevaporized hexachloropropene, 133 cc/min of hydrogen fluoride, and 62 cc/min of chlorine were passed to effect the reaction at 350° C. The produced gas was washed with water, alkali, and the water solution of the reducer, and then analyzed by gas chromatography. The results are shown in Table 2.

TABLE 2

| Product | Yield rate (%) | |
|---|---|---|
| | Example 4 | Example 5 |
| $CF_3CCl_2CF_2Cl$ | 40 | 40 |
| $CF_3CCl_2CFCl_2$ | | |
| $CF_3CCl=CFCl$ | 44 | 44 |
| $CF_3CCl=CCl_2$ | | |

Note that the by-products $CF_3 CCl_2 CFCl_2$, $CF_3 CCl=CFCl$, and $CF_3 CCl=CCl_2$ are compounds which can be reused for manufacturing the target product CFC215aa.

Example 6

Synthesis of CFC215aa through chlorofluorination of hexachloropropene by the liquid phase method (1)

29.9 g (0.1 mol) of $SbCl_5$ was placed in a condenser-equipped autoclave of 500 ml made of Hastelloy. The temperature was then gradually raised to 80° C. inside the reactor, in which HF was passed at 0.5 mol/hr for 1 hour.

With the temperature kept at 80° C., 0.5 mol/hr of hexachloropropene, 3 mol/hr of HF, and 1.0 mol/hr of chlorine were added. During the reaction, the reaction pressure was kept at 10 kg/cm². When 498 g (2 mol) of hexachloropropene was added, the reaction was stopped. After the reaction was completed, the pressure was gradually reduced and the contents were extracted.

Organic matters which were distilled during the reaction and which remained in the autoclave after the reaction were collectively analyzed by gas chromatography. The results are shown in Table 3.

Example 7

Synthesis of CFC215aa through chlorofluorination of hexachloropropene by the liquid phase method (2)

29.9 g (0.1 mol) of $SbCl_5$ was placed in a condenser-equipped autoclave of 500 ml made of Hastelloy. The temperature was then gradually raised to 60° C. inside the reactor, in which HF was passed at 0.5 mol/hr for 1 hour.

With the temperature kept at 60° C., 0.5 mol/hr of hexachloropropene, 3 mol/hr of HF, and 1.0 mol/hr of chlorine were added. During the reaction, the reaction pressure was kept at 10 kg/cm². When 498 g (2 mol) of hexachloropropene was added, the reaction was stopped. After the reaction was completed, the pressure was gradually reduced, and the contents were extracted.

Organic matters which were distilled during the reaction and which remained in the autoclave after the reaction were collectively analyzed by gas chromatography. The results are shown in Table 3.

Example 8

Synthesis of CFC215aa through chlorofluorination of hexachloropropene by the liquid phase method (3)

29.9 g (0.1 mol) of $SbCl_5$ was placed in a condenser-equipped autoclave of 500 ml made of Hastelloy. The temperature was then gradually raised to 80° C. inside the reactor, through which HF was passed at 0.5 mol/hr for 1 hour.

With the temperature kept at 80° C., 0.5 mol/hr of hexachloropropene, 3 mol/hr of HF, and 1.5 mol/hr of chlorine were added. During the reaction, the reaction pressure was kept at 10 kg/cm². When 249 g (1 mol) of hexachloropropene was added, the reaction was stopped. After the reaction was completed, the pressure was gradually reduced, and the contents were extracted.

Organic matters which were distilled during the reaction and which remained in the autoclave after reaction were collectively analyzed by gas chromatography. The results are shown in Table 3.

TABLE 3

| Product | Yield rate (%) | | |
|---|---|---|---|
| | Example 6 | Example 7 | Example 8 |
| $CF_3CCl_2CF_2Cl$ | 85 | 61 | 95 |
| $CF_3CClHCF_2Cl$ | 11 | 14 | 4 |
| $CCl_3CF=CF_2$ | 4 | 25 | 1 |

Example 9

Synthesis of 2,3,3-trichloro-1,1,1-trifluoropropene through fluorination of hexachloropropene by the vapor phase method First by the following method, $Al_2 O_3$ was fluorinated. Into a 20 mm diameter reaction tube made of Hastelloy C, 11.5 g (16 cc) of $Al_2 O_3$ in pellet form was filled. The tube was heated from room temperature, while passing nitrogen and hydrogen fluoride, gradually up to the reaction temperature. When the temperature was reached inside the system, the nitrogen was stopped, and when the temperature was stabilized, the chlorofluorination reaction was started.

Through the reaction tube filled with 11.5 g of $Al_2 O_3$ which had been fluorinated, 7 cc/min of prevaporized hexachloropropene and 95 cc/min of hydrogen fluoride were passed to effect the reaction at 300° C. The produced gas was washed with water and the water solution of alkali and then analyzed by gas chromatography. The results are shown in Table 4.

TABLE 4

| Product | Yield rate (%) |
|---|---|
| $CF_3CCl=CCl_2$ | 95 |
| $CF_3CCl_2CFCl_2$ | 3 |

Through the fluorination reaction, the by-products $CF_3 CCl_2 CFCl_2$ can be reused for manufacturing the target product. $CF_3 CCl_2 CF_2 Cl$.

Example 10

Synthesis of CFC215aa through chlorofluorination of 2,3,3-trichloro-1,1,1-trifluoropropene by the vapor phase method (1)

Through the reaction tube filled with 20 g of $Cr_2 O_3$ which was fluorinated in the same manner as in Example 4, 11 cc/min of prevaporized $CF_3 CCl=CCl_2$, 133 cc/min of hydrogen fluoride and 62 cc/min of chlorine were passed to effect the reaction at 200° C. The produced gas was washed with water, alkali and the water solution of reducer, and then analyzed by gas chromatography. The results are shown in Table 5.

Example 11

Synthesis of CFC215aa through chlorofluorination of 2,3,3-trichloro-1,1,1-trifluoropropene by the vapor phase method (2)

Through the reaction tube filled with 20 g of $Cr_2O_3$ which had been fluorinated in the same manner as in Example 4, 11 cc/min of prevaporized $CF_3$ $CCl=CCl_2$, 133 cc/min of hydrogen fluoride and 62 cc/min of chlorine were passed to perform reaction at 250° C. The produced gas was washed with water, alkali and the water solution of the reducer, and then analyzed by gas chromatography. The results are shown in Table 5.

TABLE 5

| Product | Yield rate (%) | |
| --- | --- | --- |
| | Example 10 | Example 11 |
| $CF_3CCl_2CF_2Cl$ | 30 | 88 |
| $CF_3CCl_2CFCl_2$ | 65 | 2 |
| $CF_3CCl=CFCl$ | | |
| $CF_3CCl=CCl_2$ | | |

Note that the by-products $CF_3$ $CCl_2$ $CFCl_2$, $CF_3$ $CCl=CFCl$, and $CF_3$ $CCl=CCl_2$ can be reused for manufacturing the target product $CF_3CCl_2CF_2Cl$.

Example 12

Synthesis of CFC215aa through chlorofluorination of 2,3,3-trichloro-1,1,1-trifluoropropene by the liquid phase method 29.9 g (0.1 mol) of $SbCl_5$ was placed in a condenser-equipped autoclave of 500 ml made of Hastelloy. The temperature was then gradually raised to 80° C. inside the reactor, in which HF was passed at 0.5 mol/hr for 1 hour.

With the temperature kept at 80° C., 0.5 mol/hr of 2,3,3-trichloro-1,1,1-trifluoropropene, 3 mol/hr of HF, and 1.5 mol/hr of chlorine were added. During the reaction, the reaction pressure was kept at 10 kg/cm².

When 200 g (1 mol) of 2,3,3-trichloro-1,1,1-trifluoropropene was added, the reaction was stopped. After the reaction was completed, the pressure was gradually reduced and the contents were extracted.

Organic matters which were distilled during the reaction and which remained in the autoclave after the reaction were collectively analyzed by gas chromatography. The results are shown in Table 6.

TABLE 6

| Product | Yield rate (%) |
| --- | --- |
| $CF_3CCl_2CF_2Cl$ | 93 |
| $CF_3CClHCF_2Cl$ | 6 |
| $CClCF=CF_2$ | 1 |

Example 13

Synthesis of CFC215aa through chlorofluorination of propane by the vapor phase method (1)

First by the following method, $Cr_2Cl_3$ was carried on active carbon. 1.8 g of $CrCl_3.6H_2O$ was dissolved in 12 cc of ion-exchanged water, to which 6 g (14 cc) of active carbon was added. After allowing to stand overnight at room temperature, the water content was removed by an evaporator and it was then allowed to dry another night at 120° C.

Then, active carbon carrying $CrCl_3$ was fluorinated. The catalyst thus obtained was filled into a 20 mm diameter reaction tube made of Hastelloy C. The tube was then heated from room temperature in an electric furnace, while passing nitrogen and hydrogen fluoride, gradually up to the reaction temperature (350° C.). When the temperature was reached inside the system, the nitrogen was stopped, and when the temperature was stabilized, the chlorofluorination reaction was started.

Through the reaction tube filled with 6 g of active carbon carrying $CrCl_3$ which had been fluorinated, 6 cc/min of propane, 96 cc/min of hydrogen fluoride and 66 cc/min of chlorine were passed to effect the reaction at 350° C. The produced gas was washed with water, alkali, and the water solution of reducer, and then analyzed by gas chromatography. The results are shown in Table 7.

Example 14

Synthesis of CFC215aa through chlorofluorination of propane by the vapor phase method (2)

First by the following method, $FeCl_3$ was carried on active carbon. 1.8 g of $FeCl_3.6H_2O$ was dissolved in 12 cc of ion-exchanged water, to which 6 g (14 cc) of active carbon was added. After allowing to stand overnight at room temperature, the water content was removed by an evaporator and it was then allowed to dry another night at 120° C.

Then, active carbon carrying $FeCl_3$ was fluorinated. The catalyst thus obtained was filled into a 20 mm diameter reaction tube made of Hastelloy C. The tube was heated from room temperature in an electric furnace, while passing nitrogen and hydrogen fluoride, gradually up to the reaction temperature (400° C.). When the temperature was reached inside the system, the nitrogen was stopped, and when the temperature was stabilized, the chlorofluorination reaction was started.

Through the reaction tube filled with 6 g of active carbon carrying the above $FeCl_3$ which had been fluorinated, 6 cc/min of propane, 106 cc/min of hydrogen fluoride and 55 cc/min of chlorine were passed to effect the reaction at 400° C. The produced gas was washed with water, alkali, and the water solution of reducer, and then analyzed by gas chromatography. The results are shown in Table 7.

TABLE 7

| Product | Yield rate (%) | |
| --- | --- | --- |
| | Example 13 | Example 14 |
| $CF_3CCl_2CF_2Cl$ | 40 | 43 |
| $CF_3CCl_2CFCl_2$ | 45 | 45 |
| $CF_3CCl=CFCl$ | | |
| $CF_3CCl=CCl_2$ | | |

Note that the by-products $CF_3$ $CCl_2$ $CFCl_2$, $CF_3$ $CCl=CFCl$, and $CF_3$ $CCl=CCl_2$ can be reused for manufacturing the target product $CF_3$ $CCl_2$ $CF_2$ $Cl$.

Example 15

Synthesis of 2,3,3-trichloro-1,1,1-trifluoropropene through chlorofluorination of propane by the vapor phase method:

First by the following method, $CuCl_2$ was carried on active carbon. 0.9 g of $CuCl_2$ was dissolved in 12 cc of ion-exchanged water, to which 6 g (14 cc) of active carbon was added. After allowing to stand overnight at room temperature, the water content was removed by an evaporator, and it was then allowed to dry another night at 120° C.

Then, active carbon carrying $CuCl_2$ was fluorinated. The catalyst thus obtained was filled into a 20 mm diameter reaction tube made of Hastelloy C. The tube was heated from room temperature in an electric furnace, while passing nitrogen and hydrogen fluoride, gradually up to the reaction temperature (400° C.). When the temperature was reached inside the system, the nitrogen was stopped, and when the temperature was stabilized, the chlorofluorination reaction was started.

Through the reaction tube filled with 6 g of active carbon carrying $CuCl_2$ which had been fluorinated, 6 cc/min of propane, 106 cc/min of hydrogen fluoride, and 55 cc/min of chlorine were passed to effect the reaction at 400° C. The produced gas was washed with water, alkali, and the water solution of reducer, and then analyzed by gas chromatography. The results are shown in Table 8 below.

TABLE 8

| Product | Yield rate (%) |
|---|---|
| $CF_3CCl = CCl_2$ | 84 |
| $CF_3CCl_2CFCl_2$ | 2 |

Note that the by-product $CF_3 CCl_2 CFCl_2$ is a compound which can be reused for manufacturing the target product $CF_3 CCl_2 CF_2 Cl$.

Example 16

Synthesis of HFC245fa through reduction of CFC215aa

When the 2,2,3-trichloro-1,1,1,3,3-pentafluoropropane obtained in Examples 4 to 15 was reduced with hydrogen in the same manner as described in Example 1, then 1,1,1,3,3-pentafluoropropane was obtained at the conversion yield and selectivity rates given in Example 1. When the hydrogen reduction was performed in the same manner as described in Examples 2 and 3, the same results as in Examples 2 and 3 were obtained.

The above results show that based on the methods of this invention, a starting substance, which can be obtained at relatively low cost, can be used to produce 2,2,3-trichloro-1,1,1,3,3-pentafluoropropane with a high yield rate. Many of the generated by-products can be reused as raw materials for manufacturing 2,2,3-trichloro-1,1,1,3,3-pentafluoropropane. Furthermore, 1,1,1,3,3-pentafluoropropane can be efficiently and economically manufactured since 2,2,3-trichloro-1,1,1,3,3-pentafluoropropane can be efficiently reduced to 1,1,1,3,3-pentafluoropropane.

We claim:

1. A method of producing 1,1,1,3,3-pentafluoropropane which comprises reacting 2,2,3-trichloro-1,1,1,3,3-pentafluoropropane with at least 4.5 mols of hydrogen per mol of 2,2,3-trichloro-1,1,1,3,3-pentafluoropropane in the vapor phase in the presence of a noble metal catalyst.

2. A method of producing 1,1,1,3,3-pentafluoropropane which comprises reacting hexachloropropene with hydrogen fluoride and chlorine in the vapor phase in the presence of a chromium or an aluminum catalyst, or in the liquid phase in the presence of an antimony catalyst, to obtain 2,2,3-trichloro-1,1,1,3,3-pentafluoropropane; and reacting the 2,2,3-trichloro-1,1,1,3,3-pentafluoropropane with at least 4.5 mols of hydrogen per mol of 2,2,3-trichloro-1,1,1,3,3-pentafluoropropane in the vapor phase in the presence of a noble metal catalyst.

3. A method of producing 1,1,1,3,3-pentafluoropropane which comprises reacting hexachloropropene with hydrogen fluoride in the vapor phase in the presence of an aluminum catalyst to obtain 2,3,3-trichloro-1,1,1-trifluoropropene;

reacting the 2,3,3-trichloro-1,1,1-trifluoropropene with hydrogen fluoride and chlorine in the vapor phase in the presence of at least one metal catalyst selected from a group consisting of chromium, iron, cobalt, zinc, copper and manganese, or reacting the 2,3,3-trichloro-1,1,1-trifluoropropene in the liquid phase the presence of an antimony catalyst, to obtain 2,2,3-trichloro-1,1,1,3,3-pentafluoropropane; and reacting the 2,2,3-trichloro-1,1,1,3,3-pentafluoropropane with at least 4.5 mols of hydrogen per mol of 2,2,3-trichloro-1,1,1,3,3-pentafluoropropane in the vapor phase in the presence of a noble metal catalyst.

4. A method of producing 1,1,1,3,3-pentafluoropropane which comprises reacting at least one of 2,3,3-trichloro-1,1,1-trifluoropropene, 1,2,3,3-tetrachloro-1,1-difluoropropene and 1,1,2,3,3-pentachloro-1-fluoropropene with hydrogen fluoride and chlorine in the vapor phase in the presence of at least one metal catalyst selected from the group composed of chromium, iron, cobalt, zinc, copper and manganese, or in the liquid phase in the presence of an antimony catalyst, to obtain 2,2,3-trichloro-1,1,1,3,3-pentafluoropropane; and reacting the 2,2,3-trichloro-1,1,1,3,3-pentafluoropropane with at least 4.5 mols of hydrogen per mol of 2,2,3-trichloro-1,1,1,3,3-pentafluoropropane in the vapor phase in the presence of a noble metal catalyst.

5. A method of producing 1,1,1,3,3-pentafluoropropane which comprises reacting at least one compound selected from the group consisting of propane, propylene and a partially halogenated acyclic hydrocarbon having 3 carbons, with hydrogen fluoride and chlorine in the vapor phase in the presence of at least one catalyst selected from the group consisting of chromium and iron catalysts, to obtain 2,2,3-trichloro-1,1,1,3,3-pentafluoropropane; and reacting the 2,2,3-trichloro-1,1,1,3,3-pentafluoropropane with at least 4.5 mols of hydrogen per mol of 2,2,3-trichloro-1,1,1,3,3-pentafluoropropane in the vapor phase in the presence of a noble metal catalyst.

6. A method of producing 1,1,1,3,3-pentafluoropropane which comprises reacting at least one compound selected from the group consisting of propane, propylene, and a partially halogenated acyclic hydrocarbons having 3 carbons, with hydrogen fluoride and chlorine in the vapor phase in the presence of at least one metal catalyst selected from the group consisting of aluminum, copper, cobalt, zinc and manganese, to obtain 2,3,3-trichloro-1,1,1-trifluoropropene;

reacting the 2,3,3-trichloro-1,1,1-trifluoropropene with hydrogen fluoride and chlorine in the vapor phase in the presence of at least one metal catalyst selected from the group composed of chromium, iron, cobalt, zinc, copper and manganese, or in the liquid phase in the presence of an antimony catalyst, to obtain 2,2,3-trichloro-1,1,1,3,3-pentafluoropropane;

and reacting the 2,2,3-trichloro-1,1,1,3,3-pentafluoropropane with at least 4.5 mols of hydrogen per mol of 2,2,3-trichloro-1,1,1,3,3-pentafluoropropane in the vapor phase in the presence of a noble metal.

7. A method as in any one of claims 1–6, wherein the noble metal catalyst is supported on a carrier selected from the group consisting of active carbon, alumina, silica gel, titanium oxide and zirconia.

8. A method as in any one of claims 1–6, wherein the noble metal catalyst is palladium, platinum or rhodium.

9. A method according to claim 8, wherein the noble metal catalyst is palladium.

10. A method according to claim 7, wherein the carrier contains 0.05% to 10% by weight of palladium.

11. A method as in any one of claims 1–6, wherein the reaction of 2,2,3-trichloro-1,1,1,3,3-pentafluoropropane with hydrogen is effected at a temperature of from 100° to 350° C.

12. A method of producing 2,2,3-trichloro-1,1,1,3,3-pentafluoropane which comprises reacting hexachloropropene with hydrogen fluoride and chlorine in the vapor phase the presence of at least one catalyst selected from the group consisting of chromium and aluminum catalysts, or in the liquid phase in the presence of an antimony catalyst.

13. A method of producing 2,2,3-trichloro-1,1,1,3,3-pentafluoropane which comprises reacting hexachloropropene with hydrogen fluoride in the vapor phase in the presence of an aluminum catalyst to obtain 2,3,3-trichloro-1,1,1-trifluoropropene; and reacting the 2,3,3-trichloro-1,1,1-trifluoropropene with hydrogen fluoride and chlorine in the vapor phase in the presence of at least one metal catalyst selected from the group consisting of chromium, iron, cobalt, zinc, copper and manganese, or in the liquid phase in the presence of an antimony catalyst.

14. A method of producing 2,3,3-trichloro-1,1,1-trifluoropropene which comprises reacting hexachloropropene with hydrogen fluoride in the vapor phase in the presence of an aluminum catalyst.

15. A method as in any one of claims 2, 12, 13 or 14, wherein the chromium or aluminum catalyst is supported on a carrier.

16. A method according to claim 15 wherein the carrier contains at least 0.1% by weight of the catalyst.

17. A method as in any one of claims 2, 12, 13 or 14, wherein the catalyst is fluorinated prior to reacting the hexachloropropene with hydrogen fluoride and chlorine.

18. A method as in any one of claims 2, 12, 13 or 14, wherein the hexachloropropene is reacted with hydrogen fluoride and chlorine at a temperature of from 50° to 500° C.

19. A method as in claim 18, wherein the mol ratio of hexachloropropene to hydrogen fluoride is 1:1 to 1:100, and the mol ratio of hexachloropropene to chlorine is 1:1 to 1:30.

* * * * *